(12) United States Patent
Kubota et al.

(10) Patent No.: US 7,934,868 B2
(45) Date of Patent: May 3, 2011

(54) THERMAL SENSOR AND MEASUREMENT DEVICE USING THE SAME

(75) Inventors: Akiko Kubota, Ageo (JP); Kenji Tomonari, Ageo (JP); Toshiaki Kawanishi, Ageo (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 113 days.

(21) Appl. No.: 11/632,366

(22) PCT Filed: Jun. 28, 2005

(86) PCT No.: PCT/JP2005/011791
§ 371 (c)(1),
(2), (4) Date: Jan. 12, 2007

(87) PCT Pub. No.: WO2006/008920
PCT Pub. Date: Jan. 26, 2006

(65) Prior Publication Data
US 2007/0237206 A1 Oct. 11, 2007

(30) Foreign Application Priority Data
Jul. 15, 2004 (JP) .................................. 2004-208666

(51) Int. Cl.
*G01K 17/20* (2006.01)
*G01N 25/00* (2006.01)
*G01N 25/28* (2006.01)
*G01N 25/40* (2006.01)

(52) U.S. Cl. ........................................... 374/43; 374/29

(58) Field of Classification Search ............. 374/16, 374/28, 29, 43–45, 137, 141–142, 144, 147, 374/148, 208, 100, 109, 163–164, 135–136, 101–104, 4–5; 73/73, 75, 23.32, 25.03, 25.04, 25.01
See application file for complete search history.

(56) References Cited

U.S. PATENT DOCUMENTS

| | | | | | |
|---|---|---|---|---|---|
| 3,245,260 | A | * | 4/1966 | Werner | 374/148 |
| 4,338,174 | A | * | 7/1982 | Tamura | 204/408 |
| 4,575,705 | A | * | 3/1986 | Gotcher | 338/28 |
| 4,655,076 | A | * | 4/1987 | Weihe et al. | 73/73 |
| 4,845,978 | A | * | 7/1989 | Whitford | 73/73 |
| 5,042,294 | A | * | 8/1991 | Uzzell | 73/75 |
| 5,057,436 | A | * | 10/1991 | Ball | 436/113 |
| 5,142,901 | A | * | 9/1992 | Nagawa et al. | 73/73 |

(Continued)

FOREIGN PATENT DOCUMENTS

JP 03-085433 A 4/1991

(Continued)

*Primary Examiner* — Gail Verbitsky
(74) *Attorney, Agent, or Firm* — Frommer Lawrence & Haug LLP; Ronald R. Santucci

(57) ABSTRACT

A thermal sensor in which, when an object to be measured is a water-based liquid, attachment of air bubbles to the external surface of the sensor is reduced to improve measurement accuracy. The thermal sensor has a sensing element (21a) including a heat producing body and a temperature sensing body, a resin mold (23) for sealing the sensing element (21a), and a heat transmission member (21c) for transmitting heat between the sensing element (21a) and a water-based object to be measured. A part of the heat transmission member (21c) is exposed from the resin mold (23) to form an exposed surface section. A hydrophilic film (50) formed of a silicon oxide film is applied to the exposed surface section and to that part of the surface of the resin mold which is positioned around the exposed surface section.

8 Claims, 11 Drawing Sheets

U.S. PATENT DOCUMENTS

| | | | | |
|---|---|---|---|---|
| 5,161,894 A | * | 11/1992 | Bourigault | 374/185 |
| 5,201,840 A | * | 4/1993 | Sausner et al. | 374/145 |
| 6,110,435 A | * | 8/2000 | Lehner et al. | 423/235 |
| 6,132,083 A | * | 10/2000 | Enala | 374/44 |
| 6,595,686 B2 | * | 7/2003 | Rengshausen et al. | 374/180 |
| 6,712,507 B2 | * | 3/2004 | Park et al. | 374/185 |
| 6,964,517 B2 | * | 11/2005 | Welker | 374/147 |
| 7,305,299 B2 | * | 12/2007 | Yasui et al. | 701/109 |
| 2006/0215729 A1 | * | 9/2006 | Wuester | 374/141 |
| 2007/0014327 A1 | * | 1/2007 | Faiola | 374/102 |
| 2008/0025266 A1 | * | 1/2008 | Tynderfeldt et al. | 370/337 |
| 2008/0025366 A1 | * | 1/2008 | McBurney | 374/44 |
| 2008/0202220 A1 | * | 8/2008 | Schmidt | 73/75 |
| 2008/0205478 A1 | * | 8/2008 | Sasanuma et al. | 374/44 |

FOREIGN PATENT DOCUMENTS

| | | |
|---|---|---|
| JP | 11-153465 | 6/1999 |
| JP | 11-153466 | 6/1999 |
| JP | 11-153561 A | 6/1999 |
| JP | 2000-028411 A | 1/2000 |
| JP | 2001-004422 A | 1/2001 |
| JP | 2001-020724 A | 1/2001 |
| JP | 2001-165737 A | 6/2001 |
| JP | 2002-202166 | 7/2002 |
| JP | 2002-236043 A | 8/2002 |
| JP | 2003-279395 A | 10/2003 |
| JP | 2003-302271 | 10/2003 |
| WO | WO 01/85901 A | 11/2001 |

* cited by examiner

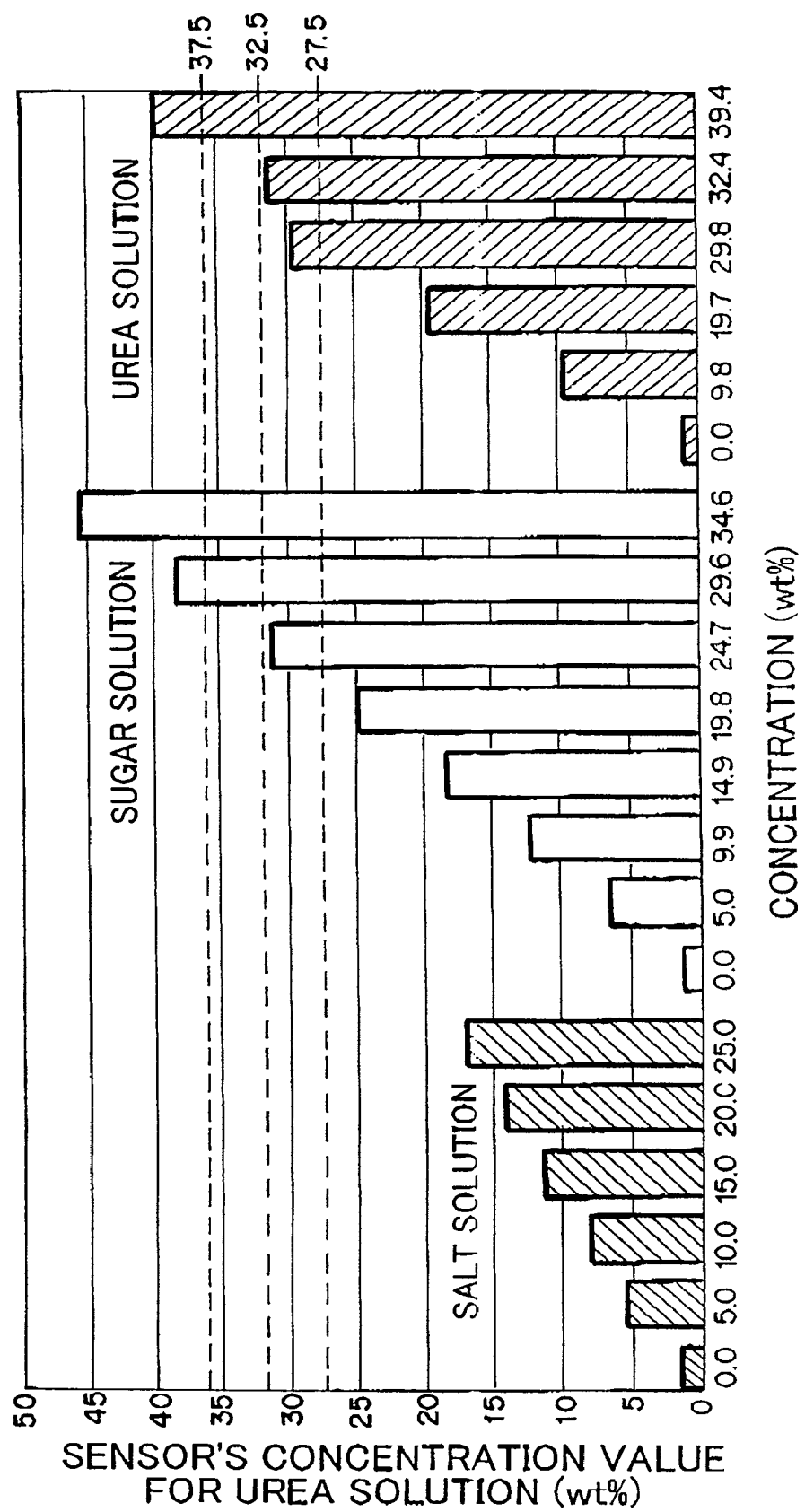

THERMAL SENSOR AND MEASUREMENT DEVICE USING THE SAME

This application is a 371 of PCT/JP2005/011791 filed on Jun. 28, 2005, published on Jan. 26, 2006 under publication number WO 2006/008920 A1 which claims priority benefits from Japanese Patent Application Number 2004-208666 filed Jul. 15, 2004.

TECHNICAL FIELD

The present invention relates to a thermal sensor which uses thermal properties of an aqueous liquid to measure the concentration of the liquid and other characteristic values thereof and a measurement device using the thermal sensor.

A thermal sensor and a measurement device can be used for measuring the urea concentration of urea solution which is sprayed to an exhaust gas purification catalyst for decomposition of nitrogen oxide (NOx) in a system for purifying exhaust gas emitted from an internal-combustion engine of, e.g., a car.

BACKGROUND ART

In an internal-combustion engine of a car, fossil fuels such as gasoline or light-oil are burned. Exhaust gas generated by the burning contains water and carbon dioxide, as well as environmental pollutants such as unburned carbon monoxide (CO), unburned carbon hydride (HC), sulfur oxide (SOx), and nitrogen oxide (NOx). In recent years, various countermeasures to purify the car exhaust gas have been taken especially for environmental protection and prevention of living environment pollution.

As one of such countermeasures, a use of an exhaust gas purification catalyst unit can be exemplified. Specifically, a three-way catalyst for exhaust gas purification is disposed in the middle of an exhaust system, and, there, CO, HC, NOx, etc. are decomposed by oxidation-reduction process to thereby render the above environmental pollutants harmless. In order to maintain the decomposition of NOx in the catalyst unit, urea solution is sprayed to the catalyst from upstream side of the catalyst unit in the exhaust system. In order to enhance the rate of decomposition of NOx, urea concentration of the urea solution should fall within a specified range, and a urea concentration of 32.5% is considered to be optimum.

The urea solution is stored in a urea solution tank installed in a car. In this state, however, concentration may change with time, or unevenness in the concentration distribution may locally occur in the tank. The urea solution which is supplied from the tank to a spray nozzle through a supply pipe by means of a pump is taken from the outlet provided near the bottom portion of the tank in general. Therefore, it is important for the urea solution in such an area to have a predetermined urea concentration, in order to enhance the efficiency of the catalyst unit.

Conventionally, measurement of the concentration of urea in the urea solution has not directly been made. Meanwhile, a technique that uses NOx sensors disposed respectively on the upstream and downstream sides of the catalyst unit in the exhaust system has been made. In this technique, it is determined whether optimum decomposition of NOx has been carried out based on the difference in NOx concentration detected by these sensors. However, this technique aims at measuring the effect of a reduction in the amount of NOx and therefore cannot determine whether or not the liquid is urea solution having a predetermined urea concentration even at the beginning of the spray of urea solution as well as before the spray. Further, the NOx sensor used in such a technique did not have sufficient sensitivity for ensuring spray of urea solution having a urea concentration falling within a predetermined range.

JP-A-11-153561 discloses a fluid identifying method. In this method, a current is applied to heat a heater, and the heat generated is used to heat a temperature sensor. Then, thermal influence is applied to heat transfer from the heater to temperature sensor using a fluid to be identified and, based on an electrical output value of the temperature sensor which corresponds to a resistance value, the type of the fluid to be identified is determined. The application of a current to the heater is periodically performed in this method.

However, although this method can distinguish among substances (e.g., water, air, and oil) having properties largely different from each other using representative values, it has difficulty determining whether or not the liquid to be measured as described above is urea solution having a predetermined urea concentration correctly and quickly.

As a typical application of the thermal sensor, measurement of mass flow rate of a liquid can be exemplified. Description of a thermal flow sensor used in such an application and a flowmeter (flow measurement device) using the thermal flow sensor is disclosed in, e.g., JP-A-11-153465, JP-A-11-153466, JP-A-2002-202166, JP-A-2003-279395, and JP-A-2003-302271.

In the case where the above-described thermal sensor, especially, an indirect-heating thermal sensor as disclosed in the above patent documents is used, if a fluid to be measured is a liquid, air and the like dissolved in the liquid is evaporated by a rise in temperature to form gas bubbles, and the gas bubbles may be adhered to the outer surface of the sensor in some cases. Further, in the case where the liquid to be measured stored in the tank has free surface in the tank, when the liquid in the tank is vibrated, the liquid surface is agitated to cause gas such as air contacting the liquid surface to be caught up in the liquid, with the result that the gas remains in the liquid as gas bubbles, and the gas bubbles may be adhered to the outer surface of the sensor in some cases.

In particular, in the case of urea solution in the tank installed in a car, severe vibration based on an external force is repeatedly applied while the car is moving, so that the adherence of the gas bubbles to the sensor outer surface becomes marked.

The adherence of the gas bubbles to the sensor prevents heat emitted from the heating element from being favorably transferred through a heat transfer member to the liquid, or prevents heat from being favorably transferred from the liquid through the heat transfer member to the temperature sensing element. When the heat transfer between the sensor and liquid to be measured is not performed normally, a large error occurs in the measurement value of the concentration of the liquid to be measured, which may result in remarkable decrease in the reliability of measurement.

DISCLOSURE OF INVENTION

The present invention has been made in view of the above situation, and an object thereof is to provide a thermal sensor that can suppress the adherence of gas bubbles to the sensor outer surface to increase the measurement accuracy and a measurement device using the thermal sensor, particularly in the case where an object to be measured is an aqueous liquid.

To achieve the above object, according to a first aspect of the present invention, there is provided a thermal sensor comprising a sensing element including a temperature sensor, a resin mold that seals the sensing element, and a heat transfer member that performs heat transfer between the sensing element and a liquid to be measured, wherein a part of the heat transfer member is exposed from the resin mold to form an exposed surface portion, and a hydrophilic membrane is formed on the exposed surface portion.

In the one aspect of the present invention, the hydrophilic membrane is a silicon oxide film. In the one aspect of the present invention, the hydrophilic membrane is formed on the surface portion of the resin mold located around the exposed surface portion of the heat transfer member. In the one aspect of the present invention, the sensing element includes a heater.

Further, to achieve the above object, according to a second aspect of the present invention, there is provided a measurement device comprising the thermal sensor having the above configuration and calculation section that calculates a characteristic value of the liquid to be measured based on the output of the thermal sensor.

In the one aspect of the present invention, a flow passage for the liquid to be measured which passes near the exposed surface portion of the heat transfer member is formed around the thermal sensor, the hydrophilic membrane is formed also on the surface portion of the member that constitutes the flow passage that faces the exposed surface portion of the heat transfer member. In the one aspect of the present invention, the liquid to be measured is urea solution, and the calculation section is configured to calculate the urea concentration of the liquid to be measured.

According to the present invention, formation of a hydrophilic membrane on the exposed surface portion of the heat transfer member exposed from the resin mold that seals the sensing element increases the wettability of the surface portion with respect to an aqueous liquid to be measured. Thus, even if air dissolved in the aqueous liquid to be measured or gas such as air contacting the aqueous liquid to be measured through its free surface becomes gas bubbles in the aqueous liquid to be measured, the gas bubbles are difficult to be adhered to the exposed surface portion of the heat transfer member. As a result, good heat transfer between sensing elements and aqueous solution to be measured can be achieved to thereby obtain high measurement accuracy.

BRIEF DESCRIPTION OF DRAWINGS

FIG. 16 is an example of a relationship between actual concentration and sensor's concentration value with respect to various liquids to be measured, wherein reference numeral 2 denotes a concentration identifying sensor section, 2a base body, 2b,2c O-ring, 2d heat transfer member cover member, 21 indirect-heating concentration detection section or indirect-heating concentration sensing section, 21a thin-film chip, 21b bonding material, 21c,22c metal fin, 21c',22c' heat transfer member, 21d bonding wire, 21e,22e external electrode terminal, 21a1 substrate, 21a2,22a2 temperature sensor, 21a3 interlayer dielectric film, 21a4 heater, 21a5 heater electrode, 21a6 protection film, 21a7 electrode pad, 22 liquid temperature detecting section or liquid temperature sensing section, 23 mold resin or resin mold, 24 introduction passage for urea solution, 4 support portion, 4a attachment portion, 6 circuit substrate, 8 circuit board cover member, 10,14 wiring, 12 connector, 50,50' hydrophilic film or hydrophilic membrane, 64,66 resistor, 68 bridge circuit, 70. differential amplifier, 71 liquid temperature detecting amplifier or liquid temperature sensing amplifier, 72 microcomputer, 74 switch, 76 output buffer circuit, 100 urea solution tank, 102 opening, 104 urea concentration identifying device, 106 inlet piping, 108 outlet piping, 110 urea solution supply pump, and US denotes a urea solution.

BEST MODE FOR CARRYING OUT THE INVENTION

An embodiment of the present invention will be described below with reference to the accompanying drawings.

Figure 1:
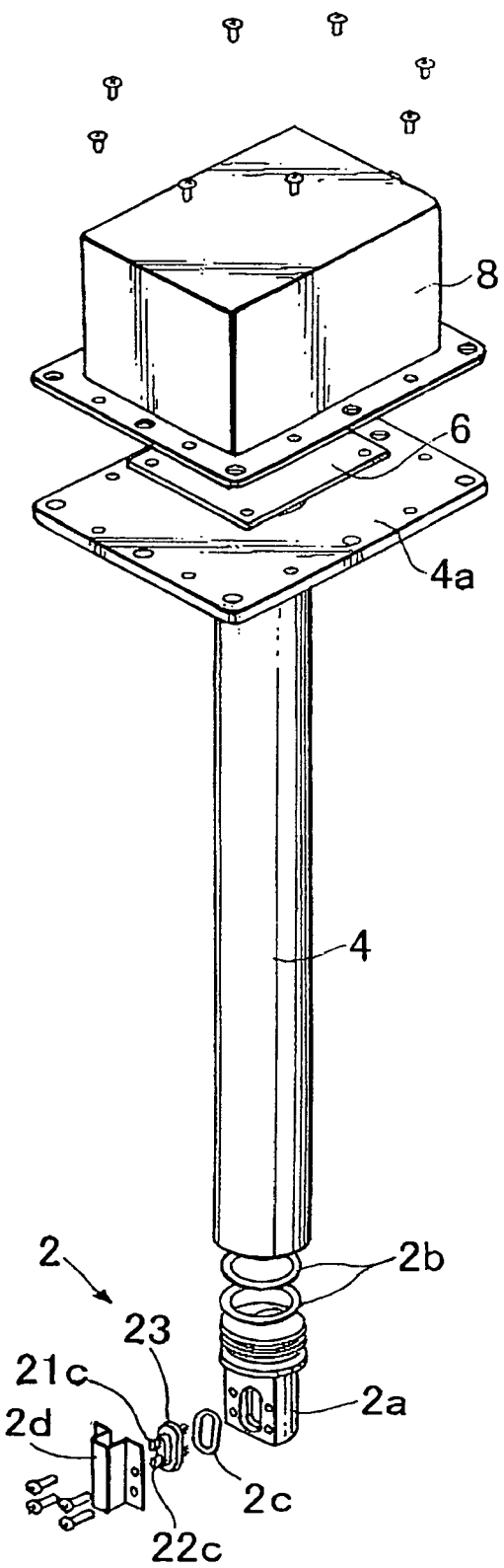
FIG. 1 is an exploded perspective view showing an embodiment of a urea concentration measurement device according to the present invention.
Figure 2:
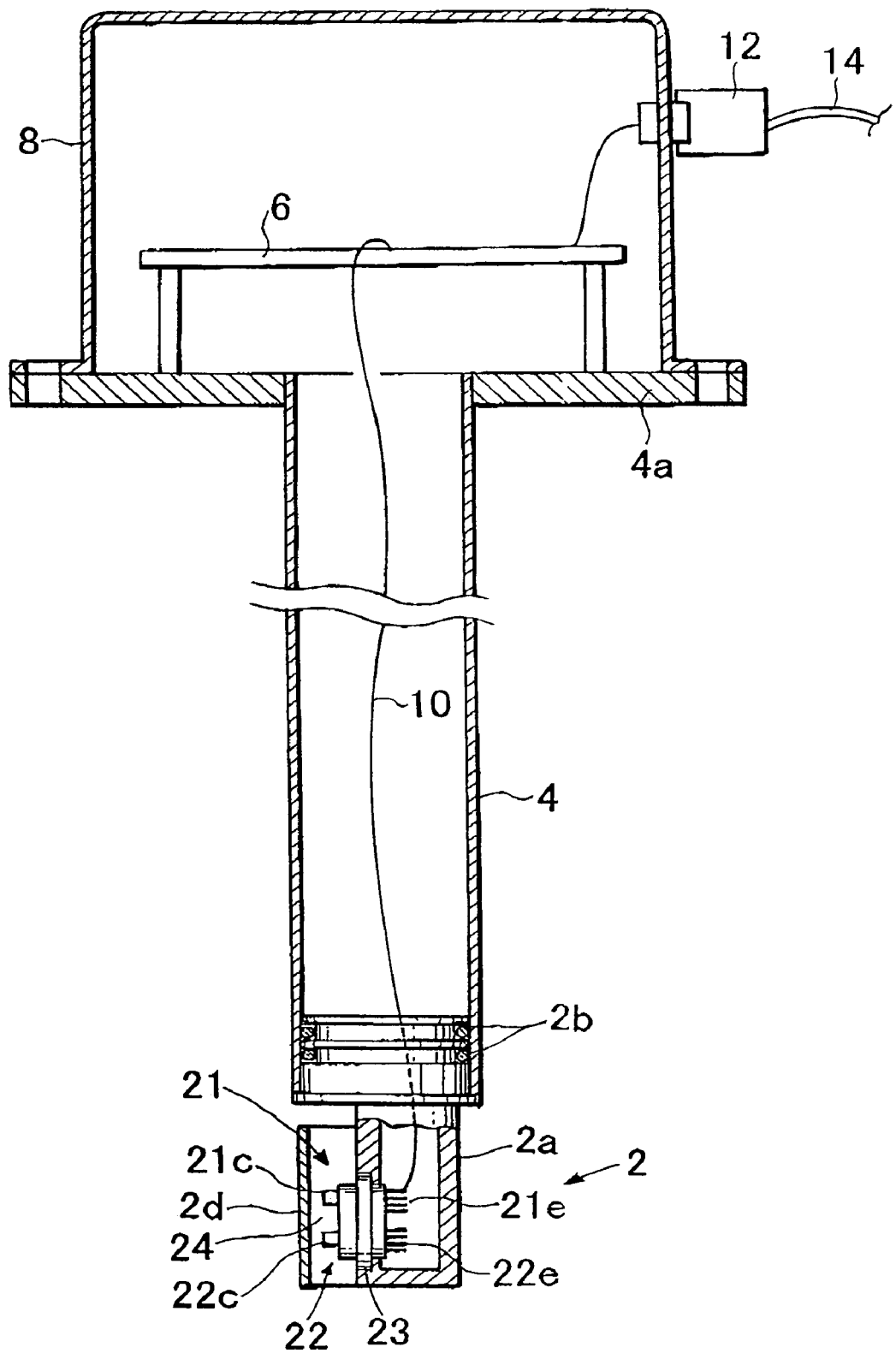
FIG. 2 is a partly omitted cross-sectional view of the urea concentration measurement device of FIG. 1.
Figure 3:
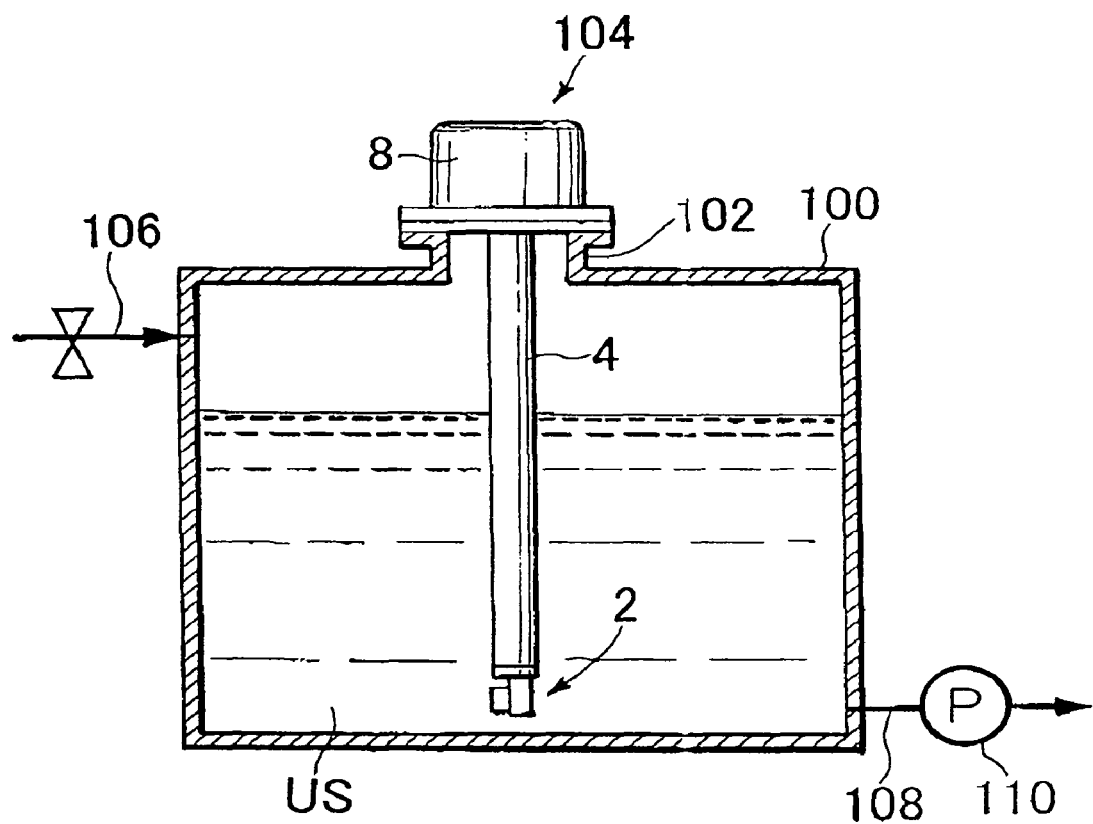
FIG. 3 is a view showing a state where the urea concentration measurement device of FIG. 1 has been set in a tank.

FIG. 1 is an exploded perspective view showing an embodiment of a thermal sensor and a measurement device using the thermal sensor according to the present invention. FIG. 2 is a partly omitted cross-sectional view of FIG. 2. FIG. 3 is a view showing a state where the thermal sensor and measurement device have been set in a tank. In this embodiment, a liquid to be measured is urea solution and the urea concentration adopted as a characteristic value of the urea solution is measured. The measurement device according to the present embodiment performs also determination whether or not detected urea concentration falls within a predetermined range (also referred to as "identification of urea solution based on urea concentration" or merely as "identification of urea concentration"). Therefore, hereinafter, urea concentration measurement or urea concentration measurement device is also referred to as "urea concentration identification" or "urea concentration identifying device".

As shown in FIG. 3, a urea solution tank 100 for NOx decomposition that constitutes an exhaust gas purification system installed in, e.g., a car has, at its upper portion, opening 102. A urea concentration identifying device 104 according to the present invention is fitted to the opening 102. The urea solution tank 100 is connected to both an inlet piping 106 through which the urea solution is introduced into the tank and an outlet piping 108 through which the urea solution is discharged from the tank. The outlet piping 108 is connected to the tank at substantially the same height position as the bottom line of the tank 100, and starts from the outlet of the tank 100 to a not shown urea solution sprayer through a urea solution supply pump 110. In an exhaust system, the urea solution is sprayed to a catalyst unit by the urea solution sprayer disposed in immediately upstream side of an exhaust gas purification catalyst unit.

The urea concentration identifying device 104 has an identifying sensor section (identifying sensor unit) 2 and support portion 4. The identifying sensor section 2 is attached to one end (lower end) of the support portion 4, and an attachment portion 4a for attachment to the tank opening 102 is attached to the other end (upper end) of the support portion 4.

Figure 4:
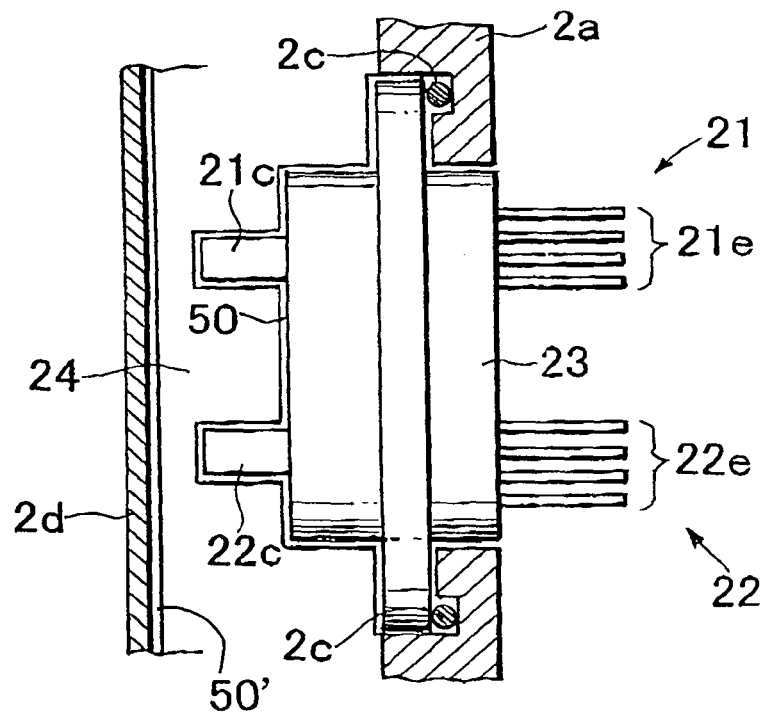
FIG. 4 is an enlarged view showing an indirect-heating concentration sensing section and a liquid temperature sensing section.
Figure 5:
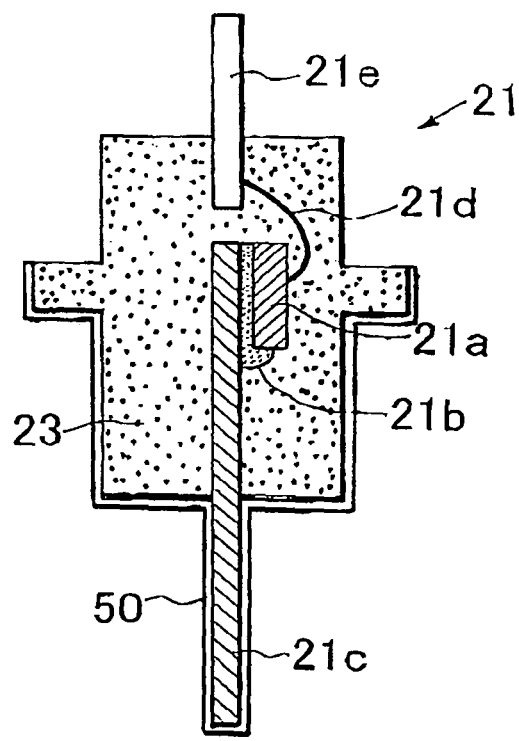
FIG. 5 is a cross-sectional view of the indirect-heating concentration sensing section of FIG. 4.

The identifying sensor section 2 has an indirect-heating concentration detection section or indirect-heating concentration sensing section 21 including a heater and temperature sensor (heat sensor) and a liquid temperature detecting section or liquid temperature sensing section 22 for detecting the temperature of a liquid to be measured. The indirect-heating urea concentration detection section 21 and liquid temperature detecting section 22 are disposed apart from each other in vertical direction by a predetermined interval. FIG. 4 shows, in an enlarged manner, the indirect-heating concentration detection section 21 and liquid temperature detecting section 22. FIG. 5 shows a cross-section of FIG. 4.

As shown in FIGS. 4 and 5, the indirect-heating concentration detection section 21 and liquid temperature detecting section 22 are integrated with each other by means of mold resin 23. As shown in FIG. 5, the indirect-heating concentration detection section 21 has a thin-film chip 21a including the heater and temperature sensor, a metal fin 21c serving as a heat transfer member for concentration detection section, which is coupled to the thin-film chip 21a by means of a bonding material 21b, and an external electrode terminal 21e electrically connected respectively to electrodes of the heater and temperature sensor of the thin-film chip 21a by means of a bonding wire 21d. The liquid temperature detecting section 22, which has the same configuration as that of the indirect-heating concentration detection section 21, has a metal fin 22c serving as a heat transfer member for liquid temperature detecting section and an external electrode terminal 22e.

Figure 6:
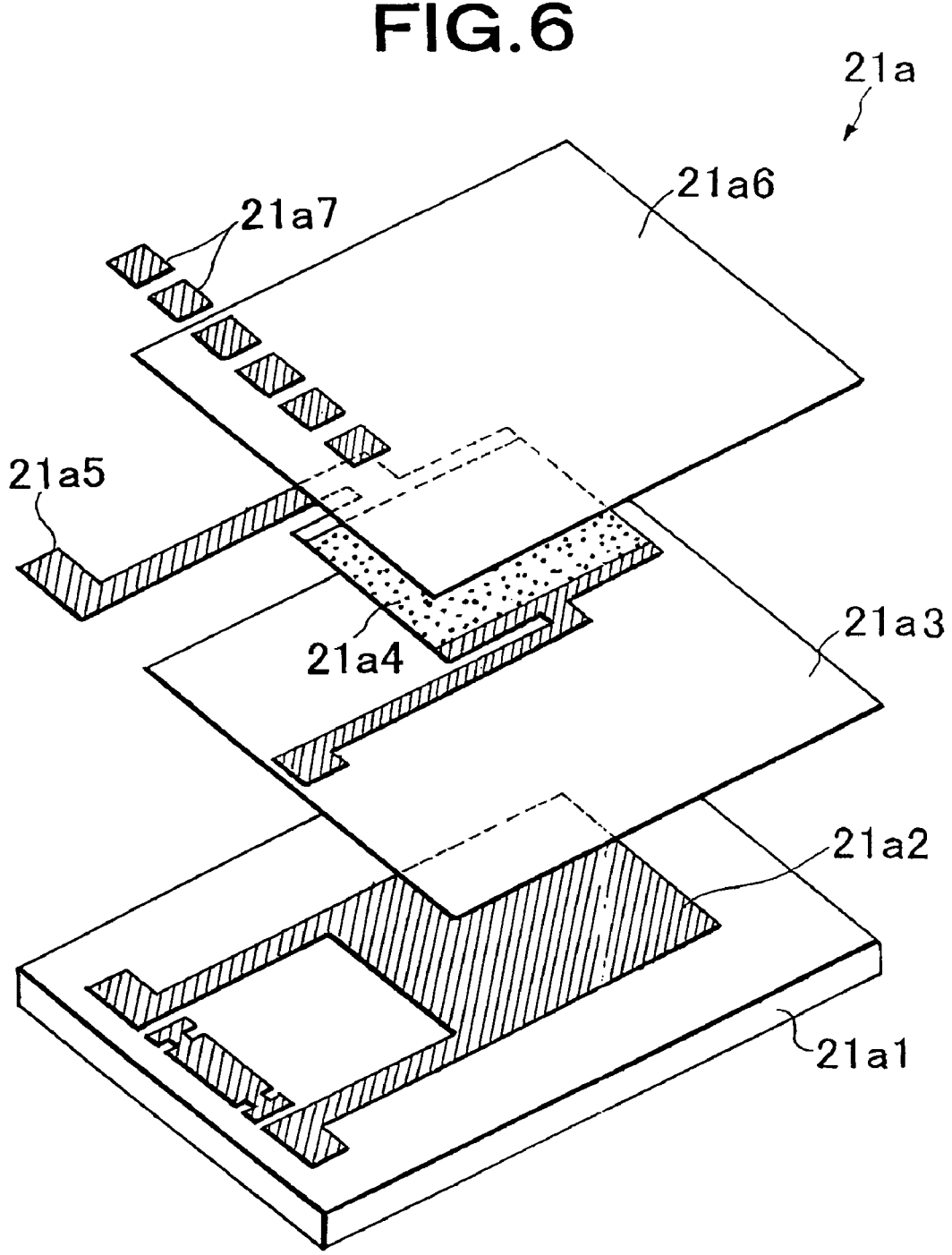
FIG. 6 is an exploded perspective view showing a thin-film chip of the indirect-heating concentration sensing section.

FIG. 6 is an exploded perspective view showing the thin-film chip 21a of the indirect-heating concentration detection section 21. The thin-film chip 21a has a laminated body in which, for example, a substrate 21a1 made of $Al_2O_3$, a temperature sensor 21a2 made of Pt, an interlayer dielectric film 21a3 made of $SiO_2$, a heater 21a4 made of $TaSiO_2$, a heater electrode 21a5 made of Ni, a protection film 21a6 made of $SiO_2$, and an electrode pad 21a7 made of Ti/Au are sequentially laminated. Although not shown, the temperature sensor 21a2 is formed in a zig-zag pattern. Although a thin-film chip 22a of the liquid temperature detecting section 22 has the same configuration as that of the thin-film chip 21a of the indirect-heating concentration detection section 21, it does not allow the heater to be active, but allows only a temperature sensor 22a2 to be active.

As shown in FIGS. 1 and 2, the identifying sensor section 2 has a base body 2a attached to the lower end of the support portion 4. When the base body 2 is attached to the support portion 4, O-rings 2b are interposed therebetween. A mold resin or resin mold 23 integrating the indirect-heating concentration detection section 21 and liquid temperature detecting section 22 is attached to the side surface of the base body 2a through an O-ring 2c. A cover member 2d is so provided to the base body 2a as to surround the metal fin 21c for liquid concentration detection section and metal fin 22c for liquid temperature detecting section. In a state where the cover member 2d has been attached to the base body 2a, an introduction passage 24 for urea solution is formed. The introduction passage 24 extends, passing through the metal fin 21c for concentration detection section and metal fin 22c for liquid temperature detecting section, in a vertical direction with its upper and lower ends opened. Further, in a state where the cover member 2d has been attached to the base body 2a, the flange portion of the mold resin 23 is pressed against the base body 2a to cause the mold resin 23 to be fixed to the base body 21a.

As shown in FIGS. 4 and 5, a part of each of the metal fins 21c and 22c is exposed from the resin mold 23 to form an exposed surface portion, and a hydrophilic film or hydrophilic membrane 50 formed on the exposed surface portion. More preferably, the hydrophilic membrane 50 is also formed on the surface portion of the resin mold 23 located around the exposed surface portions of the metal fins 21c and 22c. That is, the hydrophilic membrane 50 is formed over the exposed surface portions of the metal fins 21c and 22c and the surface portion of the resin mold 23 located around the exposed surface portions of the metal fins 21c and 22c. Note that, in FIGS. 1 and 2, the hydrophilic membrane 50 is omitted.

The hydrophilic membrane 50 is, e.g., a silicon oxide film. The thickness of the silicon oxide film 50 is, e.g., 0.01 μm to 1 μm. The silicon oxide film 50 has a good adhesiveness with both the metal fins 21c, 22c and resin mold 23 and has a high film strength. The surface of the silicon oxide film 50 has a higher hydrophilicity than the surfaces of the metal fins 21c, 22c and resin mold 23. The degree of hydrophilicity can be represented by a water contact angle. In general, water contact angle of about 40° or less is defined as hydrophilic. The water contact angle of the silicon oxide 50 can be made 40° or less and therefore the silicon oxide film 50 exhibits hydrophilicity. In the present invention, the water contact angle of the hydrophilic membrane 50 is preferably 35° or less, more preferably 30° or less, further preferably 25° or less, and most preferably 20° or less.

The silicon oxide film 50 can be formed by, e.g., a sputtering method, a CVD (chemical vapor deposition) method, or by coating application. The sputtering and CVD methods have disadvantages that it takes longer actual processing time, a large thickness film is difficult to form, and the size of a machine configuration for film formation needs to be increased. On the other hand, the coating application has many practical advantages such as simpler processing, and shorter actual processing time, except for standing time. As the coating agent to be applied, one containing organic silicon compound and with which the silicon oxide film will be formed by a reaction after application can be used. Examples of such coating agent include polysilazane containing e.g., perhydropolysilazane, silane coupling agent added according to need, organic solvent, palladium catalyst or amine catalyst added according to need (e.g., Aquamica™ available from Clariant Japan Co., Ltd.). A concrete example of the coating application and processing before and after the coating application is as follows:

(1) Ethanol cleaning process (for removal of stain on the surface on which coating agent is to be applied)

(2) Xylene cleaning process (for degreasing of the surface)

(3) Drying process (for removal of water from the surface: at about 100° C., for about one hour)

(4) Coating agent applying process (spray coating, brush or waste coating, flow coating, or immersion coating, etc.)

(5) Heating process (for solvent removal and silicon oxide conversion: at 125 to 200° C., for about one hour)

(6) Heating and humidifying process (for silicon oxide conversion: at 50 to 90° C., at 80 to 95%, for about three hours)

(7) Atmospheric cooling process

Examples of the cleaning process include one using ethanol or xylene as cleaning solvent and one using organic solvent such as acetone, isopropyl alcohol, or hexane as cleaning solvent.

In the heating process and heating and humidifying process, the following conversion reaction occurs between the coating agent and atmospheric water (naturally-occurring water or water generated during humidification) to form the silicon oxide film:

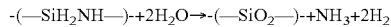

-(—SiH$_2$NH—)-+2H$_2$O→-(—SiO$_2$—)-+NH$_3$+2H$_2$

By providing the heating and humidifying process after the heating process, heating temperature in the heating process can be decreased. If the heating and humidifying process is not carried out, the heating temperature in the heating process needs to be increased to about 250° C.

The thickness of the formed silicone oxide film is, e.g., 0.01 μm to 1 μm, as described above. However, more preferably, the thickness of the silicone oxide film be between 0.05 μm and 0.8 μm because, if excessively thick, the film easily peeled off, and, if excessively thin, it becomes difficult to maintain the hydrophilicity of the film for a long time.

As shown in FIG. 2, a circuit substrate 6 that constitutes a concentration detecting circuit to be described later is disposed on the upper end of the support portion 4. A cover member 8 is so attached to the upper end of the support portion 4 as to cover the circuit substrate 6. As shown in FIG. 2, a wiring 10 electrically connecting the indirect-heating concentration detection section 21 and liquid temperature detecting section 22 of the identifying sensor section 2 to the circuit substrate 6 extends inside the support portion 4. A microcomputer that constitutes an identifying calculation section to be described later is mounted on the circuit substrate 6. A wiring 14 extends between the circuit substrate 6 and an external device through a connector 12 provided to the circuit board cover member 8 for communication between them. The identifying calculation section may be disposed outside the circuit substrate 6. In this case, the circuit substrate 6 and identifying calculation section are connected through the wiring 14.

The above-mentioned base body 2a and heat transfer member cover member 2d of the identifying sensor section 2, support portion 4, and circuit board cover member 8 are made of a corrosion-resistant material such as a stainless steel.

Figure 7:
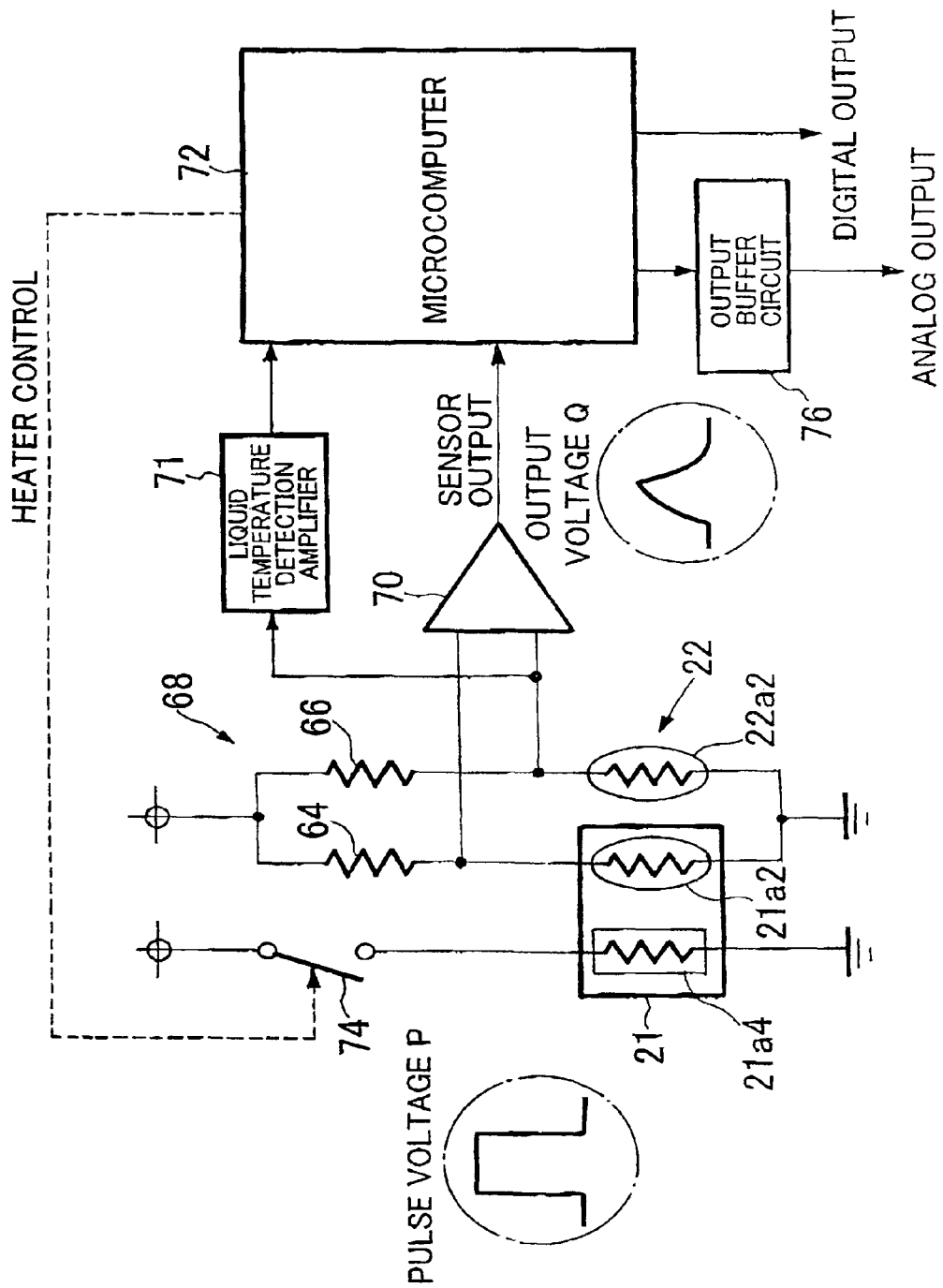
FIG. 7 is a view showing a configuration of a circuit for concentration identification.

FIG. 7 shows a configuration of a circuit for concentration identification performed in the present embodiment. The temperature sensor 21a2 of the indirect-heating concentration detection section 21, temperature sensor 22a2 of the liquid temperature detecting section 22, and two resistors 64, 66 constitute a bridge circuit 68. The output of the bridge circuit 68 is input to a differential amplifier 70, and the output of the differential amplifier 70 (also referred to as "concentration detecting circuit output" or "sensor output") is input to the microcomputer 72 that constitutes an identifying calculation section through a not shown A/D converter. Further, to the microcomputer 72, a liquid-temperature-corresponding output value which correspond to the temperature of a liquid to be measured is input from the temperature sensor 22a2 of the liquid temperature detecting section 22 through a liquid temperature detecting amplifier 71. Further, a heater control signal for controlling open/close of a switch 74 is output from the microcomputer 72 to the switch 74 disposed in a power supplying line to the heater 21a4 of the indirect-heating concentration detection section 21.

A concentration identifying operation in the present embodiment will be described below.

Firstly, the tank 100 is filled with a urea solution US and, at the same time, the introduction passage 24 for urea solution, which is formed by the cover member 2d of the identifying sensor section 2, is filled with the urea solution US. The urea solution US supplied in the tank 100 and introduction passage 24 for urea solution does not substantially flow.

The switch 74 is closed for a predetermined time period (e.g., 4 seconds) by means of the heater control signal output from the microcomputer 72 to the switch 74. Then, a single pulse voltage P having a predetermined height (e.g., 10V) is applied to the heater 21a4 to allow the heater to generate heat. An output voltage (sensor output) Q of the differential amplifier 70 at that time gradually increases while a voltage is applied to the heater 21a4 and gradually decreases after the voltage application to the heater 21a4 is ended, as shown in FIG. 8.

Figure 8:
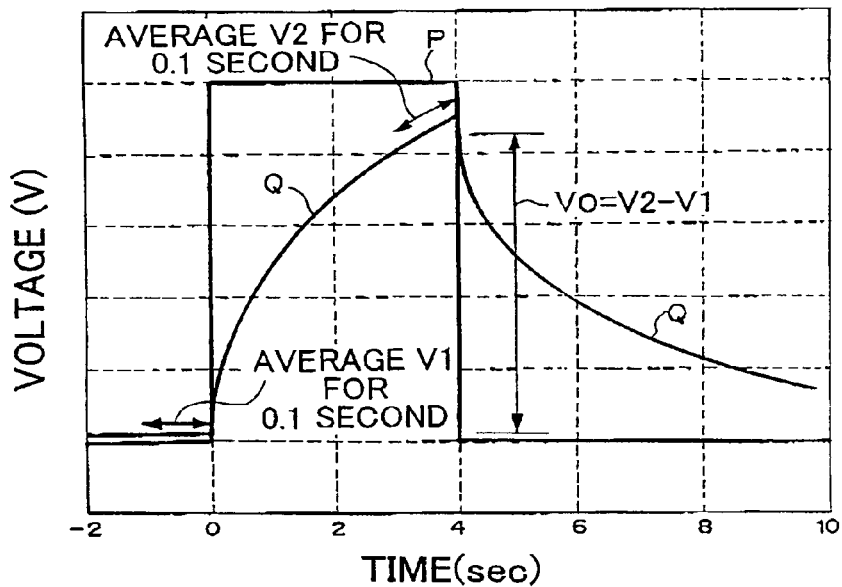
FIG. 8 is a view showing a relationship between a single pulse voltage P applied to a heater and sensor output Q.

As shown in FIG. 8, the microcomputer 72 samples the sensor outputs for a predetermined time period (e.g., 0.1 seconds) before the start of voltage application to the heater 21a4 a predetermined number of times (e.g., 256 times) and performs calculation for obtaining the average value of the sensor outputs to thereby obtain an average initial voltage value V. Further, as shown in FIG. 8, the microcomputer 72 samples the sensor outputs for a predetermined time period (e.g., 0.1 seconds) before the stop of voltage application to the heater 21a4 a predetermined number of times (e.g., 256 times) and performs calculation for obtaining the average value of the sensor outputs to thereby obtain an average peak voltage value V2. The average peak voltage value V2 corresponds to the peak temperature of the temperature sensor 21a2. After that, the microcomputer 72 obtains a difference V0 (=V2−V1) between the average initial voltage value V1 and average peak voltage value V2 as a concentration-corresponding voltage value.

Figure 9:
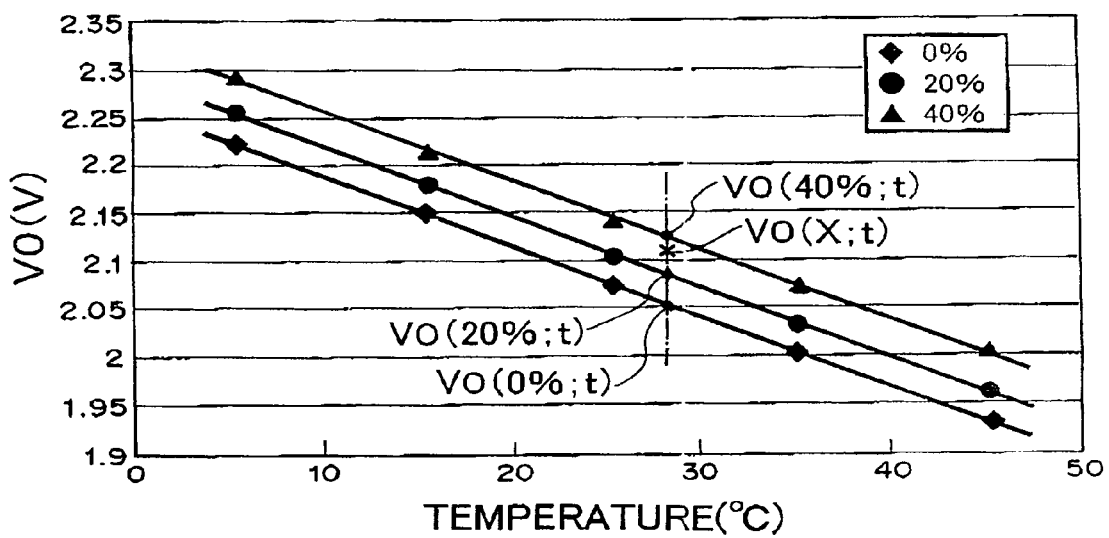
FIG. 9 is a view showing a calibration curve.

Further, a calibration curve indicating a relationship between the temperature and concentration-corresponding voltage value V0 is previously obtained with respect to some urea solutions (reference urea solutions) having a known urea solution, and the obtained calibration curve is stored in a storage means of the microcomputer 72. FIG. 9 shows an example of the calibration curve. In this example, the calibration curves of reference urea solutions having urea concentrations 0%, 20%, and 40% are shown.

Figure 10:
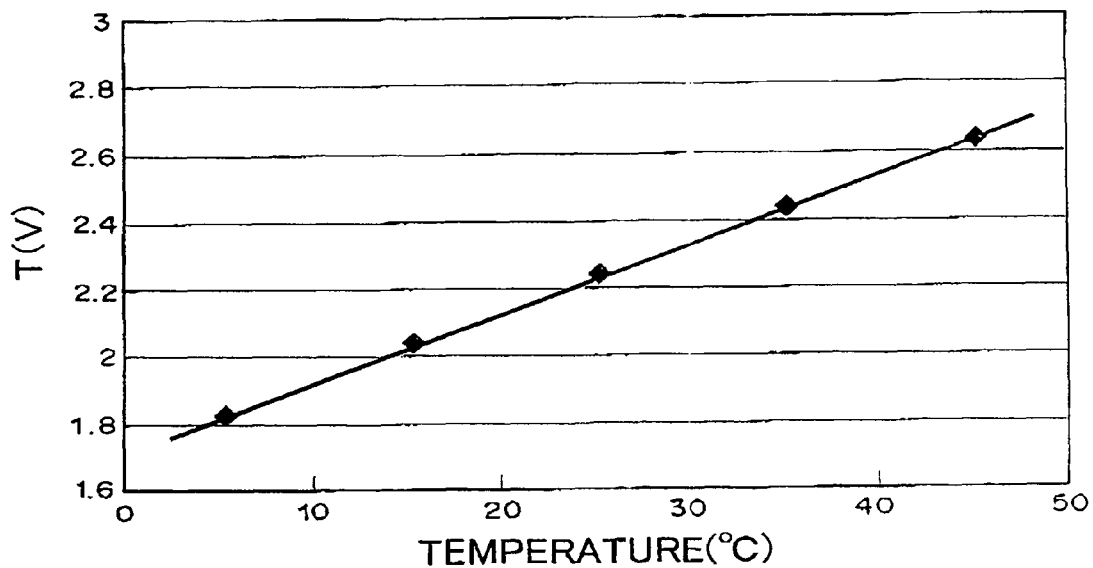
FIG. 10 is a view showing a liquid-temperature-corresponding output value T.
Figure 11:
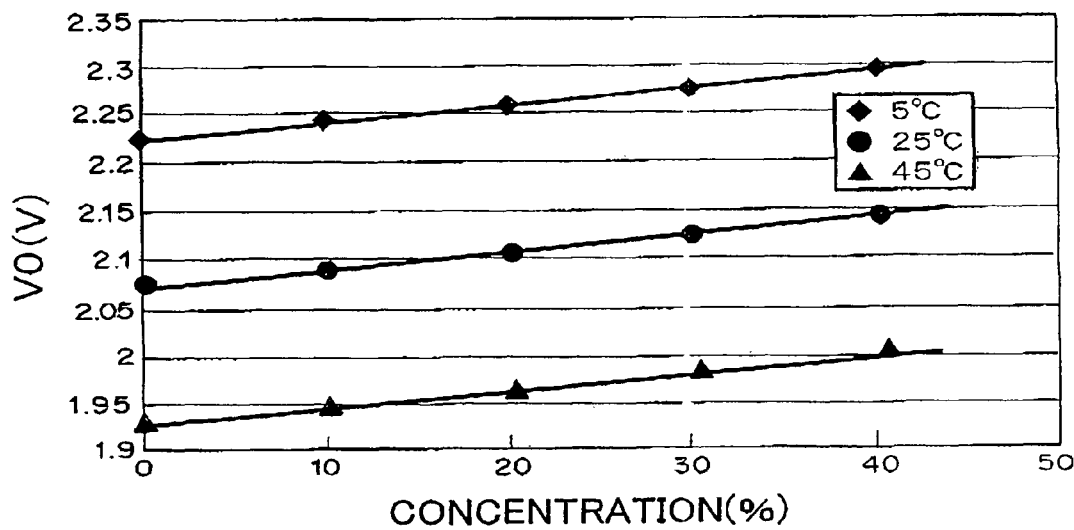
FIG. 11 is a view showing an example of a relationship between the concentration-corresponding voltage value V0 and actual concentration.

As shown in FIG. 9, the concentration-corresponding voltage value V0 changes depending on the temperature, so that when these calibration curves are used to measure the concentration of urea solution to be measured, a liquid-temperature-corresponding output value T which is input from the temperature sensor 22a2 of the liquid temperature sensing section 22 through the liquid temperature sensing amplifier 71 is also used. FIG. 10 shows an example of the liquid-temperature-corresponding output value T. Such a calibration curve is also stored in the storage means of the microcomputer 72. Further, FIG. 11 shows an example of a relationship between the concentration-corresponding voltage value V0 obtained using urea solutions having different temperatures and urea concentrations and the actual concentration.

On the calibration curve of FIG. 9, the concentration-corresponding voltage values V0 (0%; t), V0 (20%; t), and V0 (40%; t) of the respective calibration curves which correspond to the temperature value t obtained using the calibration curve of FIG. 10 based on the liquid-temperature-corresponding output value T obtained with respect to the urea solution to be measured. Then, X of the concentration-corresponding voltage value V0 (X; t) obtained with respect to the urea solution to be measured (i.e., what percent of urea concentration the X represents) is determined by performing proportional calculation using at least two (e.g., V0 (20%; t) and V0 (40%; t)) of the concentration-corresponding voltage values V0 (0%; t), V0 (20%; t), and V0 (40%; t) of the respective calibration curves. In the manner as described above, measurement and therefore identification of the urea concentration can be performed correctly and quickly (in a moment). When the calibration curves of FIG. 9 are created based on the liquid-temperature-corresponding output value T in place of the temperature, the storage of the calibration curve of FIG. 10 can be omitted.

Figure 12:
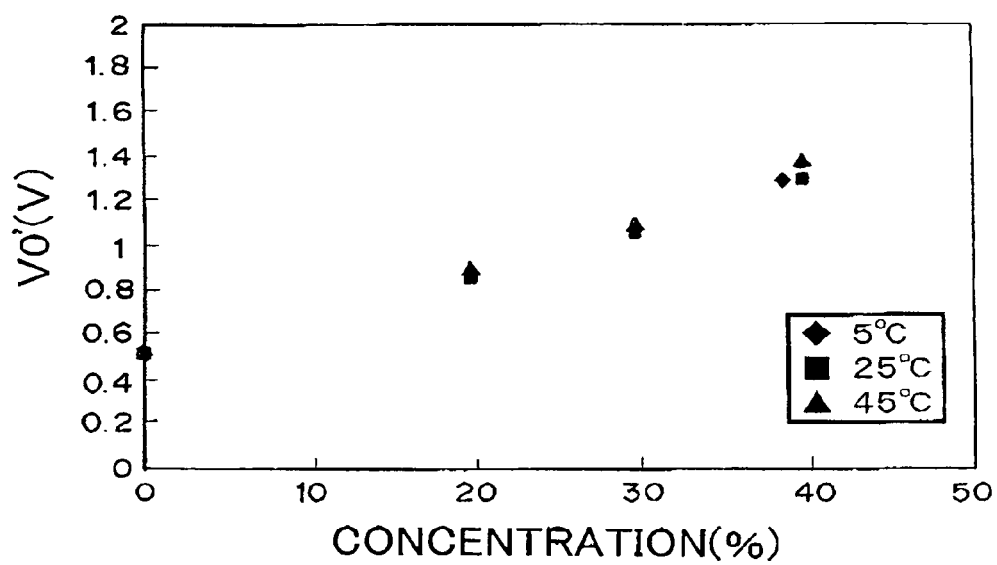
FIG. 12 shows an example of a relationship between a concentration-corresponding analog output voltage value V0' and actual concentration.
Figure 13:
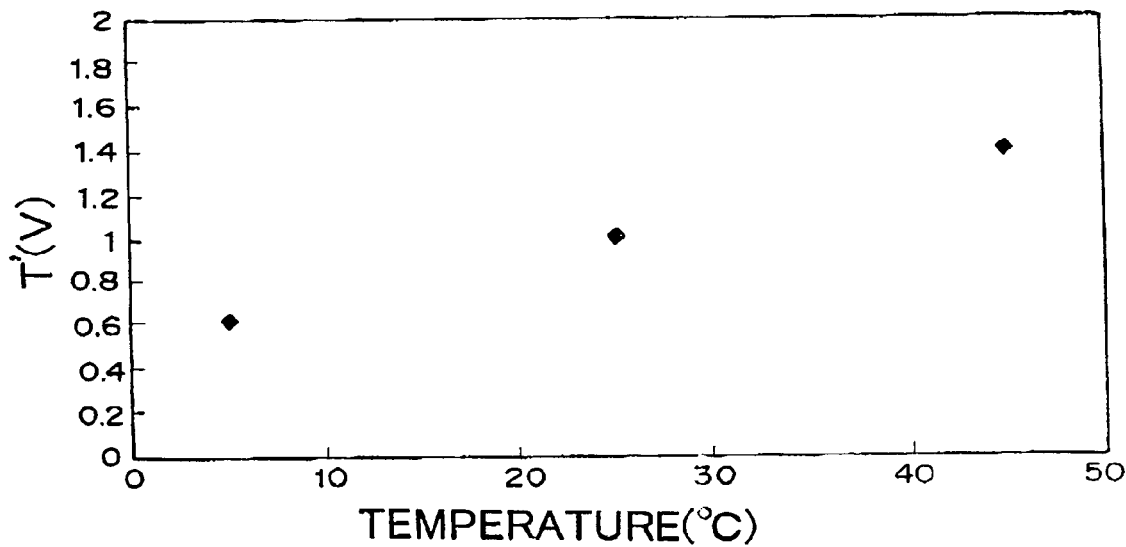
FIG. 13 shows an example showing a relationship between a liquid-temperature-corresponding analog output voltage value T' and actual temperature.

A signal indicating a concentration value obtained as described above is output to an output buffer circuit 76 shown in FIG. 7 through a not shown D/A converter. The signal is then output to a not shown main computer (ECU) that performs car engine combustion control as an analog output. FIG. 12 shows an example of a relationship between a concentration-corresponding analog output voltage value V0' and actual concentration. As can be seen from FIG. 12, no significant temperature-related difference is found between the concentration-corresponding analog output voltage value V0' and actual concentration and, therefore, the method of the present invention is practicable. FIG. 13 shows an example showing a relationship between a liquid-temperature-corresponding analog output voltage value T' and actual temperature. This liquid-temperature-corresponding analog output voltage value T' is also output to the main computer (ECU). On the other hand, signals indicating a concentration value and liquid temperature value can be taken out as a digital output according to need, and can be input to a device that performs display, alarm, and other operations.

Further, it can be considered that an alarm is issued when a decrease in the temperature of the urea solution to near the freezing temperature (about −13° C.) of the urea solution is detected based on the liquid-temperature-corresponding output value T input from the liquid temperature sensing section 22.

The urea concentration identification of the urea solution described above uses natural convection and uses a principle that there is a correlation between the kinematic viscosity of urea solution and sensor output. In order to enhance the accuracy of the liquid concentration identification, it is preferable to make a forced flow due to an external factor less likely to occur in the liquid to be measured around the fin 21c for liquid concentration sensing section and fin 22c for liquid temperature sensing section. In this regard, it is preferable to use the cover member 2d, especially, one that forms the vertical flow passage for liquid to be measured. The cover member 2d functions also as a protection member for preventing foreign matters from contacting the indirect-heating concentration sensing section 21.

As shown in FIG. 4, a hydrophilic membrane 50' is also formed on the surface of the cover member 2d (i.e., inner surface of the cover member 2d) that faces the exposed surface portions of the fin 21c for concentration sensing section and fin 22c for liquid temperature sensing section. The hydrophilic membrane 50' may be made of the same material as the hydrophilic membrane 50.

As described above, it is considered that the optimum urea concentration of the urea solution used in the exhaust gas purification system is 32.5%. Thus, a configuration may be adopted in which a urea concentration of 25% to 40% or 30% to 35% is set as an appropriate range and, when an identification result that falls outside the set appropriate range is obtained, an alarm is issued. Further, another configuration may also be adopted in which when the amount of the urea solution in the tank is decreased and thereby there remains no urea solution in the urea solution flow passage 24, a concentration-corresponding voltage value quite different from that obtained in the case where the urea concentration of the urea solution falls within the appropriate range is obtained and, also in this case, a required alarm is issued.

As described above, in the present embodiment, the hydrophilic membrane 50 is formed over the exposed surface portions of the metal fins 21c and 22c and the surface portion of the resin mold 23 located around the exposed surface portions of the metal fins 21c and 22c. Further, the hydrophilic membrane 50' is also formed on the inner surface of the cover member 2d. Therefore, it is possible to increase the wettability of these portions on which the hydrophilic membranes 50 and 50' have been formed with respect to the urea solution. Thus, if gas bubbles are generated in the urea solution, the gas bubbles are difficult to be adhered to the hydrophilic membranes 50 and 50'. Further, if the gas bubbles are adhered to the hydrophilic membranes 50 and 50', the gas bubbles are easily and quickly detached from the hydrophilic membranes due to the wettability thereof. As a result, good heat transfer between sensing elements and urea solution can be achieved to thereby obtain high measurement accuracy.

Figure 14:
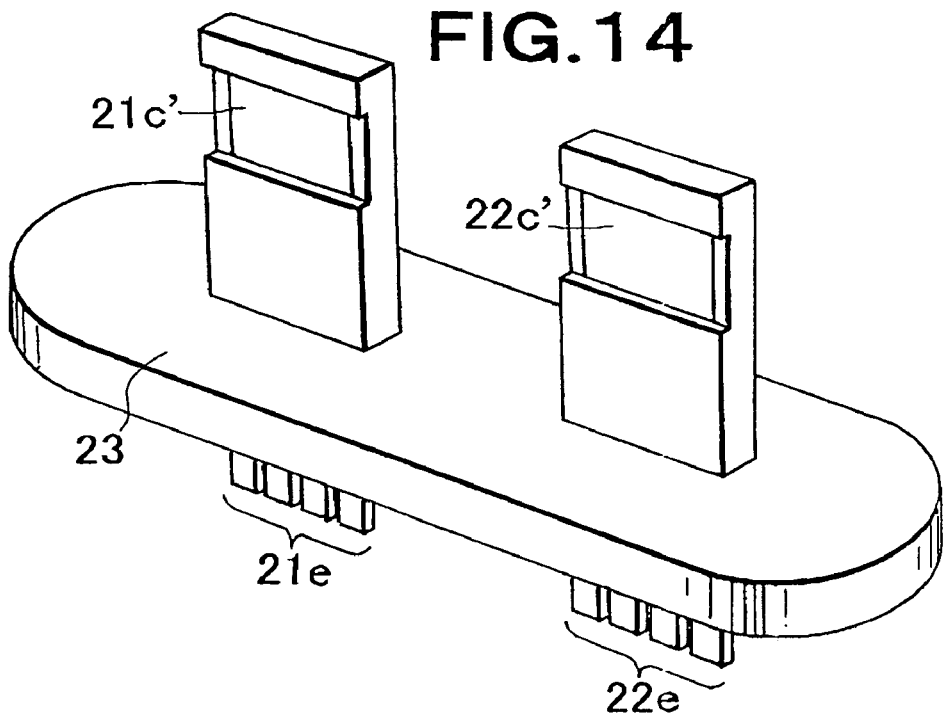
FIG. 14 is a perspective view showing another embodiment of the thermal sensor according to the present invention.
Figure 15:
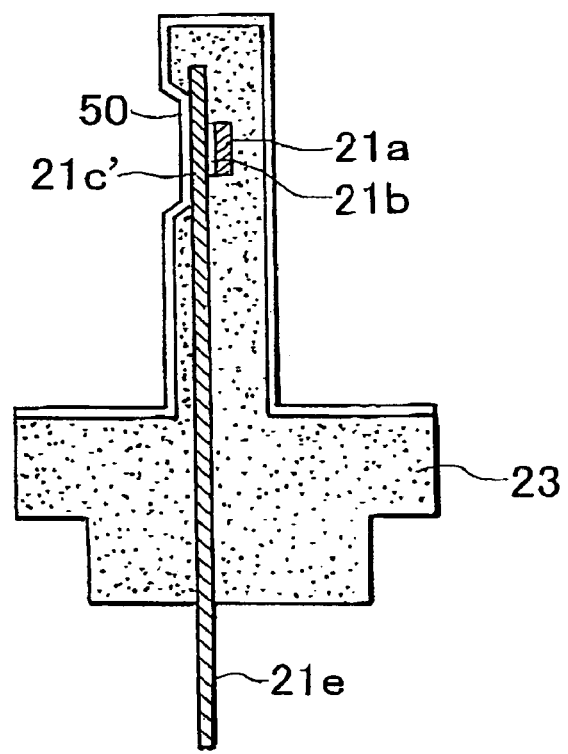
FIG. 15 is a cross-sectional view of the thermal sensor shown in FIG. 14.

FIG. 14 is a perspective view showing another embodiment of the thermal sensor according to the present invention. FIG. 15 is a cross-sectional view of FIG. 11. In FIGS. 14 and 15, the same reference numerals as those in FIGS. 1 to 13 denote the same or corresponding parts as those in FIGS. 1 to 13.

In the present embodiment, a heat transfer member 21c' for concentration sensing section and a heat transfer member 22c' for liquid temperature sensing section are not protruded outside but only the one sides thereof are exposed from the resin mold 23. As in the case of the above embodiment, the hydrophilic membrane 50 is formed on the exposed surface portions of the heat transfer members 21c' and 22c' and the surface portion of the resin mold 23 located around the heat transfer members 21c' and 22c'. Note that the illustration of the hydrophilic membrane 50 is omitted in FIG. 14

Although urea solution is used as a liquid to be measured in the above embodiments, other solutions may be used in the present invention. For example, in the case where salt solution or sugar solution is used, sensor outputs that change depending on the concentration of the salt solution or sugar solution can be obtained as shown in FIG. 16 as in the case where the urea solution is used. FIG. 16 shows an example in which a calibration curve for measurement of urea concentration of urea solution is used for obtaining the sensor outputs. However, it will be appreciated by those skilled in the art that, by using a calibration curve previously prepared with respect to the salt solution or sugar solution as in the case of the urea solution, an accurate salt or sugar concentration value can be obtained.

Further, in the above embodiments, although the concentration of a solution is adopted as a characteristic value of a liquid to be measured, the kinetic viscosity, specific gravity, and the like may be adopted in addition to the concentration in the present invention. For the measurement of the characteristic value, it is only necessary to use the calibration curve previously prepared with respect to the characteristic value in the same manner as in the case of the concentration. Further, in the above embodiment, the temperature (measured by the liquid temperature sensing section 22) is adopted as a characteristic value measured by the thermal sensor.

The present invention will be further described hereinafter with reference to an example and a comparative example.

Example

The thermal sensor of the embodiment shown in FIGS. 14 and 15 was used to prepare the urea concentration measurement device (urea concentration identifying device) of the embodiment as shown in FIGS. 1 to 13. Each of the heat transfer member 21c' for concentration sensing section and heat transfer member 22c' for liquid temperature sensing section is made of a stainless steel (SUS316L) and has a thickness of 0.3 mm. The exposed surface portion that is exposed from the resin mold has a width of 5 mm and a height of 3 mm. The resin mold 23 is made of silica and carbon-containing epoxy resin. The silicon oxide film 50 formed on the heat transfer member 21c' for concentration sensing section and heat transfer member 22c' for liquid temperature sensing section and the surface portion of the mold resin 23 located around the heat transfer members 21c' and 22c' has a thickness of 0.5 μm and a water-contact angle of 28°. The formation of the silicon oxide film 50 was performed by using Aquamica™ NL150A as follows: (1) Ethanol cleaning process, (2) Xylene cleaning process, (3) Drying process (at 100° C., for one hour), (4) Aquamica™ coating process (spray coating), (5) Heating process (at 175° C., for one hour), (6) Heating and humidifying process (at 70° C., at 90%, for three hours), and (7) Atmospheric cooling process.

The concentration identifying sensor section of the urea concentration measurement device was immersed in urea solution having a urea concentration of 32.5% end then the urea solution is heated to 35° C. A urea concentration value was obtained as an output of the measurement device one hour after the start of the heating process. The above measurement cycle was performed 10 times. Then, average of the absolute values of differences between the measurement values and actual value (32.5%) obtained in the ten times measurement was calculated. The result was 1%. The measurement accuracy was sufficiently high.

Comparative Example

The thermal sensor and urea concentration measurement device (urea concentration identifying device) were prepared in the same manner as the above Example except that the silicon oxide film 50 is not formed on the thermal sensor.

The same measurement cycle as that in the above Example was performed five times. Then, average of the absolute values of differences between the measurement values and actual value (32.5%) obtained in the ten times measurement was calculated. The result was 18%. The measurement accuracy was low.

What is claimed is:

1. A measurement device comprising:
   a thermal sensor; and
   a calculation section electrically coupled to the thermal sensor,
   wherein the thermal sensor comprises:
   a sensing element including a heater and a temperature sensor that senses heat generated by voltage application to the heater;
   a resin mold that seals the sensing element;
   a heat transfer member exposed from the resin mold that performs heat transfer between the sensing element and an aqueous liquid to be measured,
   a base body to which the resin mold is fixed; and
   a heat transfer member cover member attached to the base body and surrounding the heat transfer member so as to form therebetween a flow passage for the aqueous liquid to be measured,
   wherein a part of the heat transfer member is exposed to the flow passage so as to form a first exposed surface portion, a part of the resin mold is exposed to the flow passage so as to form a second exposed surface portion, and at least one of the first exposed surface portion, the second exposed surface portion and an inner surface portion of the heat transfer member cover member exposed to the flow passage is hydrophilic, and
   wherein the calculation section calculates a characteristic value of the aqueous liquid to be measured based on a first value of output of the thermal sensor obtained by averaging a predetermined number of samples from the output of the thermal sensor at a first predetermined time period prior to starting the voltage application and a second value of output of the thermal sensor obtained by averaging a predetermined number of samples from the output of the thermal sensor at a second predetermined time period prior to stopping the voltage application to the heater.

2. The measurement device as set forth in claim 1, wherein the first exposed surface portion, second exposed surface portion or inner surface portion which is hydrophilic has a water contact angle of not more than 35°.

3. The measurement device as set forth in claim 1, wherein the first exposed surface portion, second exposed surface portion or inner surface portion which is hydrophilic includes a hydrophilic membrane.

4. The measurement device as set forth in claim 3, wherein the hydrophilic membrane is a silicon oxide film.

5. The measurement device as set forth in claim 1, wherein the voltage application is performed by applying a single pulse voltage, and the time period is a time of applying the single pulse voltage to the heater.

6. The measurement device as set forth in claim 1, wherein the calculation section calculates the characteristic value based on the difference between the first and second values of output of the thermal sensor.

7. The measurement device as set forth in claim 1, wherein the liquid to be measured is urea solution, and the calculation section is configured to calculate urea concentration of the liquid to be measured.

8. The measurement device as set forth in claim 1, wherein the characteristic value of the aqueous liquid to be measured is at least one of values of concentration, kinetic viscosity, specific gravity and temperature of the aqueous liquid.

* * * * *